United States Patent [19]

Degironimo et al.

[11] Patent Number: 4,502,488
[45] Date of Patent: Mar. 5, 1985

[54] INJECTION SYSTEM

[75] Inventors: Bruno Degironimo, Billerica; Neil D. Silverman, Framingham; William R. Oliver, Chelmsford; Eugene C. Rideout, Billerica, all of Mass.

[73] Assignee: Allied Corporation, Morristown, N.J.

[21] Appl. No.: 457,755

[22] Filed: Jan. 13, 1983

[51] Int. Cl.³ .............................................. A61B 5/02
[52] U.S. Cl. ................................... 128/692; 128/713; 604/246
[58] Field of Search ............................ 128/691–692, 128/713, 663; 604/52–53, 246, 280, 283–284; 73/204; 137/596.17–596.18

[56] References Cited

U.S. PATENT DOCUMENTS

| 3,701,345 | 10/1972 | Heilman et al. | 128/655 |
| 3,733,899 | 5/1973 | Auphan et al. | 128/692 X |
| 3,915,155 | 10/1975 | Jacobson et al. | 128/692 |
| 3,987,788 | 10/1976 | Emil | 128/713 |
| 3,995,623 | 12/1976 | Blake et al. | 128/642 |
| 4,015,593 | 4/1977 | Elings et al. | 128/713 |
| 4,212,298 | 7/1980 | Gezari | 128/692 X |
| 4,217,993 | 8/1980 | Jess et al. | 604/246 X |
| 4,236,527 | 12/1980 | Newbower et al. | 128/692 |
| 4,267,836 | 5/1981 | Whitney et al. | 604/246 X |
| 4,300,552 | 11/1981 | Cannon | 604/246 X |
| 4,329,993 | 5/1982 | Lieber et al. | 604/280 X |
| 4,364,376 | 12/1982 | Bigham | 604/52 X |

FOREIGN PATENT DOCUMENTS 0721078  3/1980  U.S.S.R. .............................. 128/692

OTHER PUBLICATIONS

Wilson, "Application of Thermal-Electronic Instrum. to Biol. Flows", Proc. of 8th Ann. 1969 IEEE Region III Convention, 11-1969, pp. 45-50.
Weisel, R. D., et al., "Clinical Applications of Thermodilution Cardiac Output Determinations", Am. J. of Surgery, 129; Apr. 1975, pp. 449-454.
Wong, M. et al., "Loss of Indicator in the Thermodilution Technique", Catheterization and Cardiovascular Diagnosis, 4:103–109, (1978).
McCormick, J. R., "Simple Method for Measurement of Cardiac Output by Thermodilution after Cardiac Operation", J. Thorac. Cardiovasc. Surg., 78:792-795, (1979).
IL 701, Product Brochure, (1979).

Primary Examiner—Lee S. Cohen
Assistant Examiner—Angela D. Sykes
Attorney, Agent, or Firm—Lowell H. McCarter

[57] ABSTRACT

An interactive injection system for use with a catheter of the type adapted for insertion into a patient's vascular system for thermodilution measurements and the like includes a chamber for storing liquid injectate, means for connecting the chamber to the catheter lumen, and a drive for operating on the chamber to flow liquid injectate from the chamber into the lumen for discharge as a bolus from the lumen into the vascular system of a patient. In preferred embodiments, a temperature sensing probe is connected between the injection chamber and the catheter for monitoring the temperature of injectate as it is introduced into the catheter. Cooperating controller apparatus includes means for operating the drive, operator controlled inputs for selecting injectate rate and volume parameters, another operator controlled input for enabling the injector drive, an input from a sensor adapted to be located in the patient's vascular system downstream from the proximal port and operative during an injection cycle in response to a sensed deviation of output (e.g., out of specification for terminating the injection sequence, and a processor for utilizing (e.g., integrating) the sensor output to generate a cardiac output value or similar data.

12 Claims, 5 Drawing Figures

FIG 2
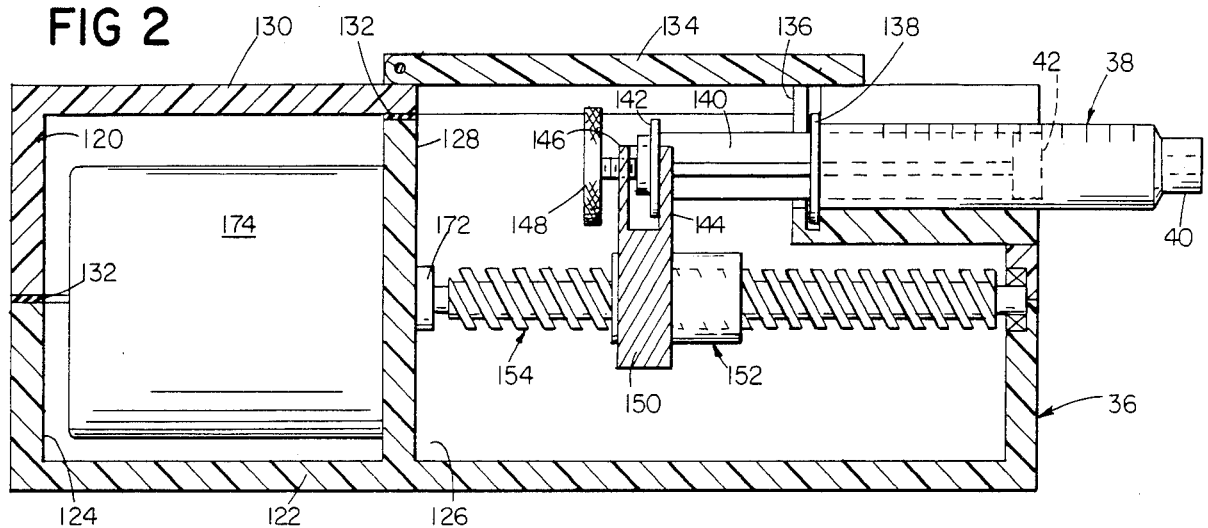
FIG 3
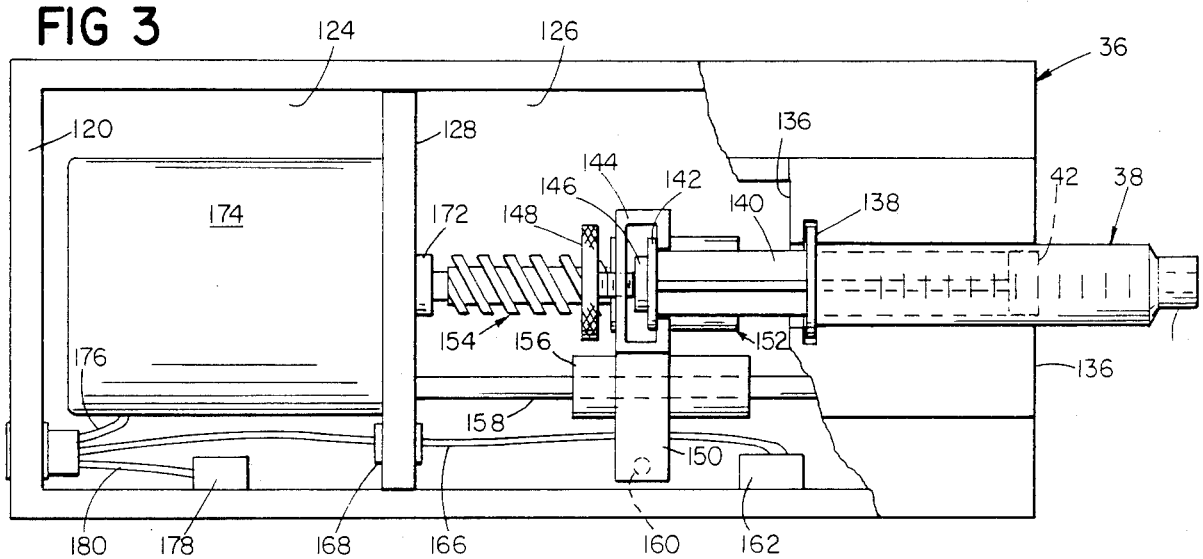
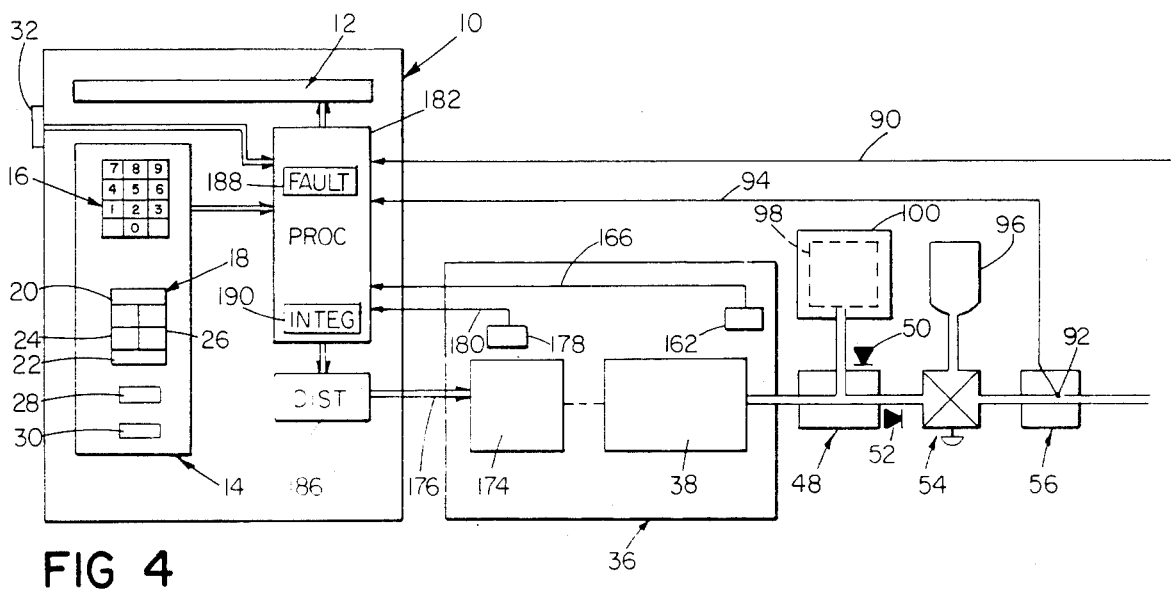
FIG 4

INJECTION SYSTEM

This invention relates to control apparatus and more particularly to injection apparatus for controlling the introduction of fluids through catheter systems for thermodilution cardiac output measurements and the like.

The importance of direct measurement of cardiac output in the case of critically ill patients has been appreciated for some time. In seriously ill patients, the probability of survival is increased if patient management is based on intensive hemodynamic monitoring. Typically, the monitoring is accomplished either by transthoracic catheter placement or by plural lumen pulmonary arterial catheterization of the flow directed type with a thermistor adjacent the tip. A bolus of liquid (typically a cold (0° C.) five percent dextrose in water solution) is introduced into the heart through the catheter and temperature is sampled in the pulmonary artery after tracer-blood mixing has occurred in the right ventricle, the sensed dynamic change in blood temperature providing an indication of cardiac output. Conventionally, the bolus of liquid is rapidly (less than five seconds) injected either manually or by pneumatic pressure (for example a carbon dioxide gun) from a preloaded syringe that is removed from cold storage just prior to injection for flow through a lumen that is in the order of fifty to eighty centimeters long and has a cross sectional area of less than one square millimeter. The quantity of injectate is a function of characteristics of the patient and the type of catheter through which the injectate is to be introduced into the patient's heart. For example, with a four lumen polyvinylchloride 7F catheter that has an outer diameter of about 2½ millimeters and an injection (CVP) lumen of about ½ millimeter square area and a passage length of about 70 centimeters to a proximal port of about 3 square millimeters area, a ten cubic centimeter volume of the cold liquid is desirably injected through that lumen into the patient's heart in about 3½ seconds for sensing by a thermistor carried by the catheter spaced about twenty-seven centimeters downstream from the proximal port. The resulting deviation from baseline temperature is integrated to provide an indication of cardiac output. Substantial pressures are required to flow the injectate through the catheter and into the patient's vascular stream, but excessive pressure can cause lumen wall failure, exposing the patient to risk, while slow injection rates distort and degrade the downstream thermal transitions which are sensed to measure cardiac output.

In accordance with the invention, there is provided an interactive injection system for use with a catheter of the type adapted for insertion into a patient's vascular system for thermodilution measurements and the like, the catheter having a lumen that extends from an external connector to a port at or adjacent the distal end of the catheter. The system includes a chamber for storing liquid injectate, means for connecting the chamber to the catheter lumen, and a drive for operating on the chamber to flow liquid injectate from the chamber into the lumen for discharge as a bolus from the lumen into the vascular system of a patient. Cooperating controller apparatus includes means for operating the drive, operator controlled inputs for selecting injectate rate and volume parameters, an input from a sensor adapted to be located in the patient's vascular system downstream from the proximal port and operative during an injection cycle in response to a sensed deviation of output (e.g., out of specification) for terminating the injection sequence, a processor for utilizing (e.g., integrating) the sensor output to generate a cardiac output value or similar data, and another operator controlled input for enabling the injector drive. In preferred embodiments, the drive is of the electromechanical type and a temperature sensing probe is connected between the injection chamber and the catheter for monitoring the temperature of injectate as it is introduced into the catheter.

In a particular embodiment, the system includes a controller unit that includes an output display, an operator interface with a keyboard type input for entering numerical values and control values, a second input for entering preset volume and rate values, a processor, and a sensor interface. The processor responds to data entry and control commands such as start and stop and to signals from the keyboard (including entered patient data such as identification number, height, weight, mean arterial blood pressure and the like) for calculating cardiac parameters such as cardiac input, systemic vascular resistance, left ventricular stroke work index, and the like; and also includes a fault monitor for monitoring thermal sensors at the proximal and distal ends of the catheter, an integrator control that responds to an 'inject' command, and a pulse distributor that responds to signals from the processor. Coupled to the controller unit is an injection chamber unit that includes a cylinder and piston arrangement and an electromechanical piston drive mechanism that includes a limited torque stepper motor, a lead screw, and an anti-backlash nut that is mechanically coupled to the piston. The stepper motor is housed in a sealed compartment separate from the injection chamber in an arrangement in which the leakage current to the patient does not exceed ten microamperes and the patient circuit isolation from earth ground circuit withstands a 2500 volt peak. The injection chamber unit is coupled to a catheter with a temperature sensor at the lumen inlet. After the operator enters parameters (catheter size and injectate volume) either through the keyboard or through the preset control, depression of the start button causes the processor and distributor to generate a series of pulses that drives the stepper motor to retract the piston and fill the chamber with the predetermined volume of injectate (typically in the range of 1–10 cubic centimeters) that volume being withdrawn from a storage container maintained at about 0° C. temperature. The system then pauses (allowing inspection of the chamber for air bubbles which must be dislodged prior to continuing the cycle) and upon actuation of an injection control (which is of a "fail safe" type in that it must be maintained actuated for the duration of the injection portion of the cycle), the bidirectional stepper motor is again energized by the controller to flow the predetermined quantity of injectate from the chamber into the catheter lumen at a uniform rate and in less than four seconds for flow into the patient's heart. Throughout the injection cycle, the controller monitors the upstream and downstream sensors and interrupts the injection cycle upon detection that either sensor is out of specification (e.g., short or open circuit). As the injectate flows through the heart and into the pulmonary artery, the downstream sensor monitors the change in temperature and transmits those signals to the processor for integration (the integration commencing a predetermined time after actuation of the injection control) and calculation of the cardiac output value which is then displayed.

The invention provides a versatile interactive injection system with operator input and sequence controls and sensor feedback to the controller for accurate injection of a precise, operator selectable volume of injectate at a rapid but pressure-limited rate and with coordinated integration that enhances the safety and accuracy of the measurement, is simple to operate, and in which detection of a defective sensor or other monitored condition interrupts the injection cycle.

Other features and advantages will be seen as the following description of a particular embodiment progresses in conjunction with the drawings, in which:

FIG. 2 is a sectional view of the injector component of the system shown in FIG. 1;

FIG. 3 is a top view (with portions broken away) of the injector component;

FIG. 4 is a block diagram of the injection control system shown in FIG. 1; and

DESCRIPTION OF PARTICULAR EMBODIMENT

Figure 1:
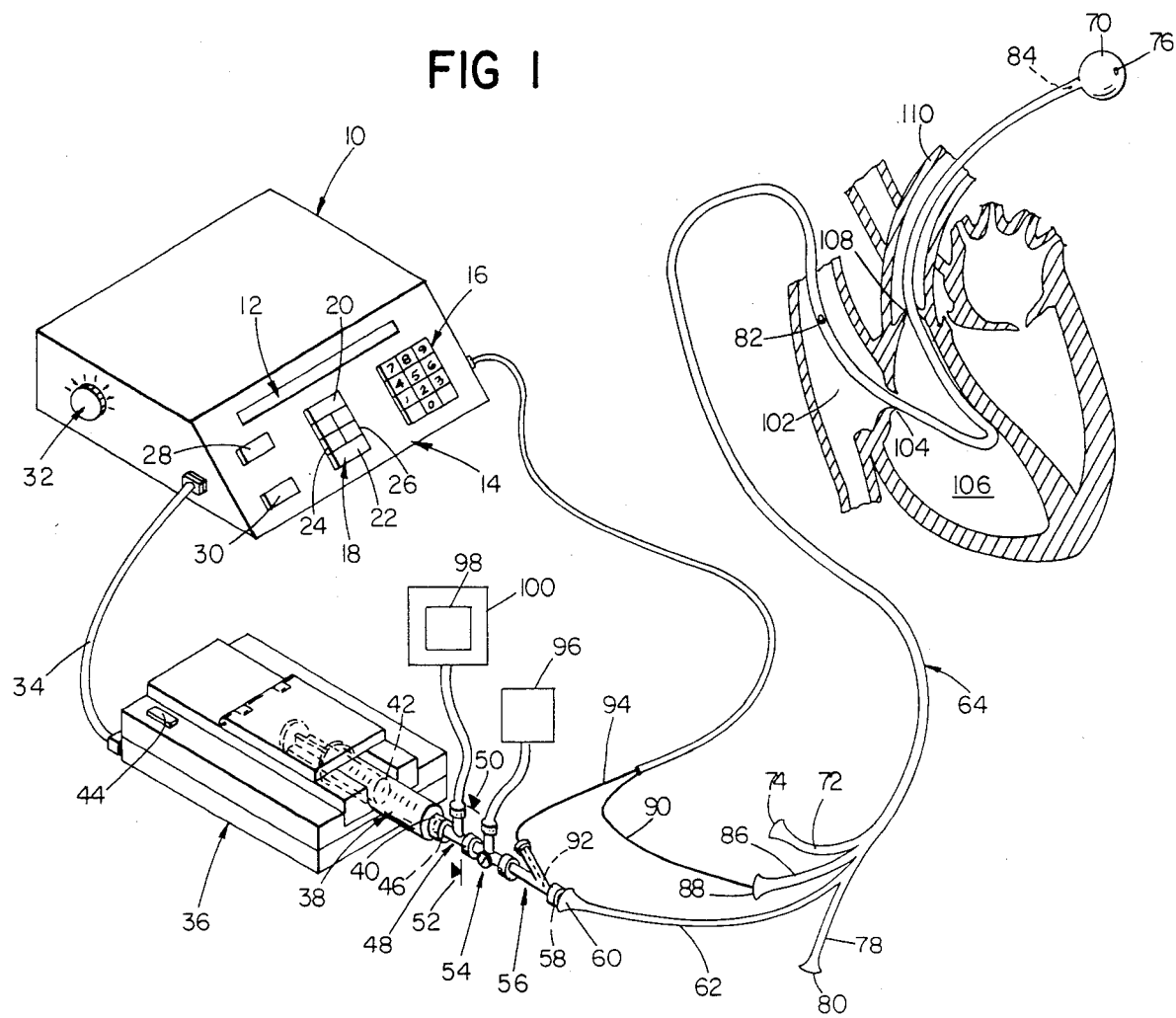
FIG. 1 is a diagrammatic view of an injection control system in accordance with the invention.

Shown in FIG. 1 is a thermodilution cardiac output measurement system that includes controller component 10 that has a display 12; a keyboard 14 with a numeric pad 16, a set of control keys 18 that includes a temperature key 20, an enter key 22, an alternate mode key 24, and a delete data key 26, a start control 28 and a stop control 30; and a thumbwheel control 32 that enables selection of preprogrammed injectate volumes as a function of particular (5F and 7F) catheters. A particular 7F catheter, for example, has a length of about one-hundred ten centimeters and a diameter of about $2\frac{1}{2}$ millimeters while a particular 5F catheter has a length of seventy centimeters and a diameter of about two millimeters. Coupled to controller 10 by means of cable 34 is injector apparatus 36 that includes cylindrical injection chamber 38 with outlet port 40 and piston 42 arranged by axial movement within cylinder 38. An operator control 44 is mounted on the injector unit 36.

Coupled to outlet 40 by Luer lock connector 46 is T adapter 48 that includes check valves 50, 52, a stop cock 54 and a flow through probe unit 56. Connected to probe unit 56 via connector 58 is coupling 60 of the CVP lumen 62 of a a four lumen catheter 64. The catheter has an expansible balloon 70 at its distal end which is expanded by pressure applied through lumen 72 and coupling 74; a distal port 76 which is connected through a second lumen 78 to coupling 80; a proximal port 82 which is connected through lumen 62 to coupling 60; and a temperature sensor (thermistor) 84 which is coupled through a fourth lumen 86 to coupling 88 which in turn is connected via line 90 to controller 10. Similarly, temperature sensor 92 of flow through probe 56 is connected via line 94 to controller 10. Connected to stop cock 54 is a source of IV fluuid 96 and connected to T adapter 48 is a source 98 (a 500 milliliter collapsible bag) of injectate in cold pack reservoir 100 that maintains the temperature of the injectate at about 0° C.

In use, catheter 64 is introduced into the vascular system of the patient at a convenient location and is advanced with balloon 70 deflated into the right atrium 102 of the patient's heart. Balloon 70 is then inflated by application of pressure through coupling 74 and the flow of blood through the heart rapidly propels the inflated balloon tipped catheter 64 from the right atrium through tricuspid valve 104 into the right ventricle 106, then through pulmonary valve 108 into the pulmonary artery 110. The inflated balloon advances the tip (distal opening 76) of catheter 64 through the pulmonary artery 110 into what is generally referred to as the pulmonary capillary wedge position. In this position, sensor 84 is disposed within the pulmonary artery 110 and the proximal flow port 82 is positioned within the right atrium 102.

With catheter 64 so positioned, a variety of diagnostic procedures may be performed, including the use of proximal port 82 for taking pressure measurements from the right atrium, for injecting or infusing solutions, or for taking blood samples; and the use of distal port 76 for sampling, infusion or injection, or measurement of pulmonary artery and pulmonary capillary wedge pressures. In thermal dilution measurements, a bolus of sterile cold injectate solution (for example, 5% dextrose in water) is injected by injector unit 36 into right atrium 102 through port 82 and cardiac output is calculated based on the resulting change in blood temperature as sensed by thermistor 84.

Further details of the injector unit 36 may be seen with reference to FIGS. 2 and 3. That unit includes housing 120 with base 122 which defines motor compartment 124 and drive assembly compartment 126 with upstanding bulkhead 128 between them. Cover member 130 is seated on base 122 and carries seals 132 that provide isolation between electrical components mounted in compartment 124 and the injection compartment 126. Cover member 130 carries hinged lid 134 which, in closed position, overlies an access opening to compartment 126 which permits access to the syringe 38. That syringe is received in a removable gib or cradle 136 that receives flange 138 for axial positioning of syringe 38. The injector chamber unit 38 can be easily replaced as desired and different size cradles can be interchanged for accepting different size injection chambers. The shaft 140 of the injection chamber syringe piston 42 has a flange 142 that is received in a coupling clevis 144 and secured by clamp plate 146 that is operated by thumbwheel 148. Clevis 144 is a portion of frame 150 to which an anti-backlash nut 152 is secured which in turn is mounted on lead screw 154 of pitch such that one revolution of screw 154 produces an axial movement of about 0.5 centimeter of nut 152 and the clevis unit 144. Also carried by frame 150 is guide 156 which is mounted for axial movement on fixed rod 158 to provide axial guidance for the driven frame 150. Frame 150 also carries indicator 160 which cooperates with a "home" Hall effect sensor 162. Signals from sensor 162 are applied over cable 166 through seal grommet 168 carried by bulkhead 128 into motor compartment 124. Lead screw 154 is connected via coupling 172 that passes through bulkhead 128 to bi-directional 4.3 volt, 65 inch ounce stepper motor 174 which turns lead screw 154 one revolution for every two-hundred stepping pulse signals that are applied to motor 174 over signal cable 176.

The injection drive system that includes stepping motor 174, lead screw 154 and drive nut 152 is engineered so that the drive system provides drive pressures of up to 96 psi to piston 42. Should chamber resistance be greater than 96 psi, motor 174 stalls as its torque output is exceeded. Mounted in motor compartment 124 is switch 178 which provides outputs over lines 180 via cable 34 to control unit 10.

With reference to the block diagram shown in FIG. 4, programmed system operating parameters as a function of catheter type and injectate quantity are selected and entered into processor 182 via thumbwheel 32. As indicated above, other operating parameters may be entered into processor 182 by keyboard 14. Processor 182 also receives signals from sensor 84 over line 90, from flow through sensor 92 over line 94, from sensor 162 over line 166, and a control signal from switch 178 over line 180; and applies signals to the pulse distributor circuit 186 to transmit control pulses over line cable 176 for operation of stepping motor 174. Processor 182 includes computer logic (INTEG 188) for integrating temperature data from sensor 84 over line 90 (the integration interval being coordinated with injection control 44 and responding to the signal over line 180 so that that interval commences about two seconds after that control is actuated) and calculating cardiac output values for output to display 12, a fault monitor (FAULT 190) which monitors the signals from probes 84 and 92 over lines 90, 94 respectively during the injection and data acquisition cycles, and other devices such as a printer.

The display 12 initially displays the instruction "press enter". Injection parameters are entered either from the thumbwheel 32 or from the keyboard 14. The desired type of the analysis may also be entered (baseline to baseline integration being normally selected but 60% integration may be selected by depression of alternate mode key 24). Injection parameter data is entered (a 7F catheter has a dead space volume ($V_d$) of 0.7 cc and a 5F catheter has a dead space volume ($V_d$) of 0.3 cc), and the computer logic calculates the K factor:

$$K = \frac{(V_i - V_d)}{9.3} \times 0.825$$

where $V_i$ = volume of injectate, and $V_d$ = volume of catheter dead space, and sets distributor 186 to generate pulses at a corresponding rate—the distributor 186 typically generating pulses at a rate of 4.6 milliseconds per step to provide an injection rate of 2.86 cubic centimeters per second for a 7F catheter, and generating stepping pulses at a lower stepping pulse rate of 7.9 milliseconds per step to provide an injection rate of 1.6 cubic centimeter per second for a 5F catheter. (With a 75 centimeter long 2F catheter, temperature sensor 84 is separate from the catheter.)

After the injection parameter data has been entered, start button 28 is depressed to begin a cardiac output cycle. In response, controller 10 displays the patient's temperature with the flashing word "inject", and stepper motor 174 is driven by pulses from distributor 186 at a relatively slow (but less than ten seconds) rate to fill chamber 38 with the selected volume of injectate from source 98, check valve 50 opening in response to negative pressure to connect source 98 to injector outlet port 40. During the cycle, the fault monitor portion 188 of processor 182 monitors the signals from probes 84 and 92 over lines 90, 94 respectively and if a "fault" (open or short circuit of either probe) is detected, processor 182 activates display 12 to display a "fault" indication and interrupts the injection cycle. Otherwise during a cardiac output measurement cycle, the patient's temperature is displayed live with an indication that the cycle is in progress. When the chamber 38 has been filled with the programmed volume of injectate, motor 174 is deenergized (pause) with opportunity for the operator to inspect the chamber 38 for air bubbles. Any detected air bubble is dislodged manually and when the injectate is clear, the operator depresses button 44 to operate switch 178 and generate a signal over line 180 to cause distributor 186 to generate a sequence of pulses at the selected rate and to initialize integrator 190 to commence the integration interval after a brief delay. The pulses from distributor 186 drive motor 174 in the injection direction, rotating lead screw 154 and advancing nut 152 to advance the piston 42 and inject the withdrawn injectate volume at the preselected rate (typically, in the range of 1–4 cubic centimeters per second). Integrator 190 commences integration after a brief time delay (principally as a function of the catheter length) so that integration is coordinated with injection.

Figure 5:
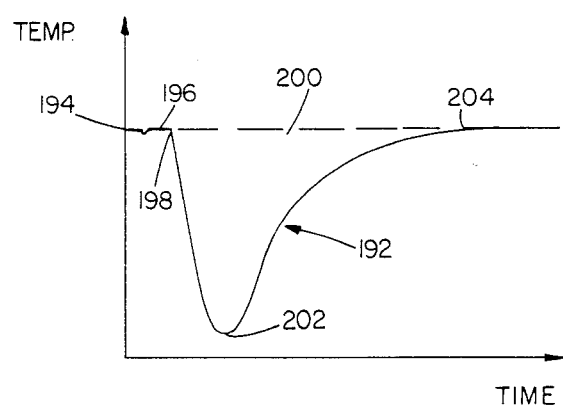
FIG. 5 is a graph indicating a cardiac output measurement sequence with the system shown in FIG. 1.

During injection, injectate temperature is monitored by sensor 92 in flow through probe 56. The injectate flows through catheter lumen 62 and is discharged through proximal port 82. The injected bolus flows from port 82 into the right atrium of the heart and through the heart into the pulmonary artery for flow past sensor 84. The curve 192 of FIG. 5 indicates graphically the change in temperature produced by that injectate. Injection commences at the zero mark (point 194) in response to a signal on line 180, and integration commences at point 196. The leading edge of a ten milliliter bolus of cold injectate flows into the right atrium. Shortly thereafter (point 198) (less than three seconds after switch 178 is closed), temperature in the pulmonary artery starts to decline, and reaches a maximum deviation from base line 200 at valley 202 in about six seconds. The temperature returns to base line (point 204) and stabilizes after about twenty seconds with a complete return to the base line in about one minute, the pulmonary arterial temperature change (from base line 200 to valley 202) being less than one degree Centigrade. The integration portion 190 of processor 182 commences integration of the temperature value between curve 192 and base line 200 at a predetermined time (point 196) after and in response to closure of switch 178, thus coordinating the integration interval with injection, and terminates when the temperature returns to base line (point 200) (or as alternately programmed as at sixty percent as indicated above). Base line fluctuations of temperature are in synchronism with respiration. The integrated temperature value above the curve 192 between points 198 and 204 provides an indication of cardiac output (C.O.) in accordance with the equation:

$$C.O. = \frac{1.08 \, (K) \, (60) \, V_i \, (T_B - T_i)}{1000 \int_0^\infty \Delta T_B(t) dt}$$

where $$1.08 = \frac{\text{Density} \times \text{Specific Heat (5\% Dextrose in Water)}}{\text{Density} \times \text{Specific Heat (Blood)}}$$

K = Correction factor (Heat absorbed by injectate and not measured by thermistor).
60 = Seconds per minute
$V_i$ = Volume of injectate (ml).
$T_B$ = Initial blood temperature (°C.).
$T_i$ = Lowest injectate temperature (°C.).
1000 = ml per liter $$\int_0^\infty \Delta\, T_B(t)dt = \text{Integral of change of blood temperature with time}$$

After integration, the calculated cardiac output value is shown at display 12.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. An interactive injection system comprising
 a catheter of the type adapted for insertion into the vascular system of a patient for thermodilution measurements or the like, said catheter having a proximal end, a distal end, a lumen that extends from said proximal end to said distal end, an external connector at said proximal end, a port adjacent said distal end of said catheter, and a thermal sensor located between said port and said distal end, said sensor providing signals as a function of temperature,
 bolus injection apparatus including a chamber for storing liquid injectate, said chamber having an outlet port, means for connecting said chamber outlet port to said lumen through said external connector, and
 drive means including a stepper motor for decreasing the effective volume of said chamber at a predetermined rate to discharge a predetermined quantity of liquid injectate from said chamber for injection through said lumen and discharge as a bolus from said port into the vascular system of the patient, said drive means including pressure responsive means for stalling said stepper motor to interrupt the decrease in volume of said chamber in response to a predetermined resistance to flow of injectate from said chamber, and
 controller apparatus including
 processor means including a pulse distributor for applying stepping pulses to said motor, means to vary the distribution of said stepping pulses to change the rate at which injectate is discharged from said chamber,
 first operator controlled input means for selecting the quantity of injectate to be discharged from said chamber,
 second operator controlled input means for applying pulses from said pulse distributor to said stepper motor for actuating said stepper motor to decrease the effective volume of said chamber at a predetermined rate to discharge said predetermined quantity of liquid injectate from said chamber for injection into the vascular system of the patient through said lumen,
 means responsive to signals from said sensor for generating output data as a function of sensed changes in response to injection of said liquid bolus through said catheter lumen into said vascular system, and
 output means for presenting output data generated by said processor means.

2. The system of claim 1 and further including third operator controlled input means for drawing said predetermined quantity of injectate into said chamber from an external reservoir.

3. The system of claim 1 wherein said chamber includes a cylinder and a piston disposed in said cylinder for axial movement therein, and said drive means is coupled to said piston, said drive means moving said piston to decrease the volume of said chamber.

4. The system of claim 3 wherein said drive means stalls in response to a sensed resistance at the outlet port of said chamber of about one hundred pounds per square inch to interrupt discharge of injectate from said chamber.

5. The system of claim 1 wherein said chamber has a transparent portion such that the quantity and quality of injectate therein may be observed by the operator.

6. The system of claim 5 wherein said stepper motor is housed in a compartment that is sealed from said chamber and is electrically isolated from said chamber so that the electrical leakage current to the patient does not exceed ten microamperes.

7. The system of claim 1 and further including fault sensitive means responsive to said sensor for interrupting discharge of injectate from said chamber in response to a sensed sensor defect.

8. An interactive injection system comprising
 a catheter of the type adapted for insertion into the right ventricle of a patient's heart by way of the vena cava for thermodilution measurements and the like, said catheter having a proximal end, a distal end, a lumen that extends from said proximal end to said distal end, an external connector at said proximal end, a port adjacent said distal end of said catheter, and a thermal sensor located between said port and said distal end for providing signals as a function of temperature,
 bolus injection apparatus including a chamber for storing liquid injectate, said chamber having an outlet port, means for connecting said chamber outlet port to said lumen through said external connector, and drive means including a stepper motor for decreasing the effective volume of said chamber at a predetermined rate to discharge a predetermined quantity of liquid injectate from said chamber for injection through said lumen and discharge as a bolus from said port into the vascular system of a patient, said stepper motor stalling when the catheter resistance to discharge of said liquid from said chamber exceeds about one hundred pounds per square inch to interrupt flow of injectate from said chamber into said catheter,
 controller apparatus including pulse distributor means for applying pulses to said stepper motor for operating said drive means, processor means responsive to signls from said sensor for controlling said drive means and for calculating a cardiac output value as a function of sensed temperature changes in response to injection of said liquid bolus into said vascular system, and output means for displaying the resultant calculated cardiac output value,
 first operator controlled input means for selecting the quantity of injectate to be discharged from said chamber,
 second operator controlled input means for actuating said injection apparatus to discharge injectate from said chamber into said lumen of said catheter, and
 third operator controlled input means for varying the distribution rate of said stepping pulses to change the rate at which injectate is discharged from said chamber.

9. The system of claim 8 and further including fourth operator controlled input means for drawing the volume of injectate selected by said first operator controlled input means into said chamber from an external reservoir.

10. The system of claim 9 wherein said chamber includes a cylinder and a piston disposed in said cylinder for axial movement therein, and said drive means is coupled to said piston, said drive means moving said piston to increase the volume of said chamber to draw injectate into said chamber from said external reservoir and to decrease the volume of said chamber to discharge injectate from said chamber.

11. The system of claim 10 for use with a plural lumen catheter that has one lumen which provides a bolus flow path to said port, and further including a second sensor at said proximal end of said catheter and means for transmitting signals from said thermal and second sensors to said processor means.

12. The system of claim 11 wherein said processor means includes delay means responsive to said second operator controlled input means for commencing integration over an interval of time of the departure from base line of temperature sensed by said thermal sensor carried by said catheter and fault sensitive means responsive to either of said sensors for interrupting discharge of injectate from said chamber in response to a detected sensor defect.

* * * * *